United States Patent
Wagner et al.

(10) Patent No.: US 8,386,196 B2
(45) Date of Patent: Feb. 26, 2013

(54) METHOD FOR DETERMINING THE WEAR STATE

(75) Inventors: Stefan Wagner, Bad Honnef (DE); Cyrus Barimani, Königswinter (DE); Günter Hähn, Königswinter (DE)

(73) Assignee: Wirtgen GmbH (DE)

( * ) Notice: Subject to any disclaimer, the term of this patent is extended or adjusted under 35 U.S.C. 154(b) by 593 days.

(21) Appl. No.: 12/584,279

(22) Filed: Sep. 2, 2009

(65) Prior Publication Data

US 2010/0076697 A1    Mar. 25, 2010

(30) Foreign Application Priority Data

Sep. 3, 2008 (DE) .......................... 10 2008 045 470

(51) Int. Cl.
*G01B 3/44* (2006.01)
*E21B 12/02* (2006.01)
*E21C 25/10* (2006.01)
*E01C 23/16* (2006.01)

(52) U.S. Cl. ............... 702/34; 175/39; 299/106; 404/94

(58) Field of Classification Search .................... 702/34, 702/40, 81, 84, 127, 150–153, 155–159, 702/167, 172, 179, 182–183, 189; 29/242–243; 299/79.1, 85.1, 101–103, 106, 110; 175/39–41, 175/379, 381–382, 401; 404/83, 86, 89, 404/93–94, 103, 122, 124

See application file for complete search history.

(56) References Cited

U.S. PATENT DOCUMENTS

2005/0207841 A1* 9/2005 Holl et al. ....................... 404/94

FOREIGN PATENT DOCUMENTS

| AT | 382 683 B | 8/1985 |
| DE | 32 18 754 C2 | 11/1983 |
| DE | 34 11 892 C2 | 10/1985 |
| DE | 35 05 408 A1 | 8/1986 |
| DE | 38 18 213 A1 | 11/1989 |
| DE | 100 15 005 A1 | 10/2001 |
| DE | 102 03 732 A1 | 8/2003 |
| DE | 10 2005 016 346 B3 | 4/2005 |

OTHER PUBLICATIONS

Liang et al., Vision-Based Automatic Tool Wear Monitoring System, Jun. 25-27, 2008, Proceedings of the 7th World Congress on Intelligent Control and Automation, Chongqing, China, pp. 6031-6035.*

* cited by examiner

*Primary Examiner* — Toan Le
(74) *Attorney, Agent, or Firm* — Waddey & Patterson, P.C.; Lucian Wayne Beavers

(57) ABSTRACT

This invention relates to a method for determining a wear state of a chisel, a chisel holder, and/or a chisel holder replacement system equipped with a chisel and chisel holder. For this method to give the user qualitative and quantitative information about the wear, according to one embodiment of this invention, a position of at least one point of the chisel and/or the chisel holder is determined by a contactless measurement method and a corresponding measurement result is compared in a switching unit to a reference value stored in a memory device.

44 Claims, 9 Drawing Sheets

METHOD FOR DETERMINING THE WEAR STATE

BACKGROUND OF THE INVENTION

When stripping road surfaces by milling and when removing mineral deposits with surface miners likewise by milling, the tools used, in particular milling chisels, are subject to a continuous wear process. When the tools reach a certain wear state, it is advisable to replace them or the efficiency of the remainder of the process decreases. In this connection, it is necessary to differentiate among different wear states that lead to the replacement of a milling chisel or chisel holder.

Replacement of the chisel may be needed because there is no longer sufficient wear material, particularly hard metal at the tip. The penetration resistance becomes too great, causing the efficiency to decrease, such as from excessive frictional loss. The wear is for the most part rotationally symmetrical.

Replacement of the chisel holder may be needed because the wear limit is reached and the holder begins to wear at the contact surface between the chisel and the holder. This wear is usually symmetrical.

Non-rotationally symmetrical wear may appear on the chisel tip and/or on the chisel head due to insufficient rotational motion of the chisel during the milling process. This results in a poor milling pattern as well as the risk of tool breakage since the supporting action of the chisel head is lost.

The chisel holder can also be subject to additional non-rotationally symmetrical wear.

The chisel may also need replacement because of breakage.

Furthermore, worn and/or broken chisels can lead to secondary damage to the chisel holders and worn chisel holders can lead to secondary damage to the milling roller. A prompt replacement of the chisels and/or chisel holders is thus necessary and reduces costs. By contrast, it is not optimal from a cost standpoint for the chisels and/or chisel holders to be replaced too early because the chisels and chisel holders, as wearing parts, are very expensive. This results in failure to properly utilize remaining wear potential. Up to now, the wear state of chisels and chisel holders is ascertained through visual inspection by the machine driver. In order to do so, the machine driver must shut down the machine or switch off the engine and decouple the roller from the drive train. The driver must then open the rear roller flap in order to visually inspect the milling roller.

The milling roller is then rotated by a second drive unit in order to permit inspection of the entire milling roller. The task of roller inspection can also be performed by a second operator. In this case, the wear state of the chisel holders is usually determined by known wear markings. The wear state of the chisels is determined by longitudinal wear and the rotational symmetry of the wear pattern.

Inspecting the wear state of the chisels and holders is very time-consuming and is also unproductive because no production can take place during this time. The entire process is interrupted, thus additionally reducing availability. Furthermore, due to the fact that the assessment is very prone to subjectivity, there is the risk of failure to optimally utilize the wear potential of the holders and chisels.

German Patent Reference DE 102 03 732 A1 discloses an apparatus in which operation can be optimized by monitoring operating states of machine components that are directly or indirectly involved in the milling process. Thus among other things, the wear state of the chisels is assessed by evaluating various machine parameters and characteristic values. During operation of the milling machine, one problem arises if the milling process and the subsurface itself, whose properties fluctuate widely, have a large influence on the evaluation of the operating state of components. Because of the widely fluctuating properties of the subsurface to be milled, it is not easy to differentiate between changing operating states of machine components directly or indirectly involved in the milling process that are attributable to changing surface properties and those that are attributable to changing tool properties.

Austrian Patent Reference AT 382 683 B discloses a mining machine in which the cutting roller is monitored in a contactless fashion. In this case, photoelectric detectors are used, which detect the presence of the chisels. This method is unable to provide a quantitative wear evaluation.

SUMMARY OF THE INVENTION

One object of this invention is to provide a method of the type mentioned above but in which it is possible to carry out a quantitative wear detection.

This object is attained if the position of at least one point, referred to below as the "position value", of the milling tool, in particular of the chisel and/or the chisel holder, is determined by a measurement method and this measurement result is compared in a switching unit to a reference value stored in a memory device.

According to this invention, the comparison of the position value to the reference value is used to establish a reference value that includes quantitative information about the wear on the milling tool, in particular on the chisel and/or chisel holder. It is then possible to evaluate the extent of wear, which assists the user with decision-making. It is thus possible for the user to decide whether a tool replacement must be carried out or whether the wear state permits continuation of a current milling task. This makes it possible to achieve a significant improvement in efficiency.

The reference value can be a value that is known in advance, such as a value that is determined and stored, or can be a characteristic field or a functional correlation with which one or more position values or calculations of them each is compared.

According to one possible embodiment of this invention, the position of the chisel tip can be detected as a position value.

In the simplest case, the position of the chisel tip relative to the center of motion of the milling roller is measured and compared to a reference value determined, for example, when the holder and chisel are new. This directly yields the longitudinal wear on the chisel and holder. When a certain limit wear length is reached, the chisel is replaced.

Alternative to an absolute measurement relative to the center of motion of the milling roller or another point of origin, it is also possible to perform a relative measurement based on at least two position values, such as on the chisel. If the points are selected so that one position value in the vicinity of the chisel tip is established and the at least one other position value is positioned in a region that is subject to only slight wear or to no wear at all, then the longitudinal wear can be directly determined as the difference between the two position values in comparison to the reference value that corresponds to the difference between the two points when the chisel is new.

If the reference value for the chisel tip is established again after each chisel replacement, then it is also possible to thereby determine the holder wear. In this context, however, it is necessary to use chisels whose lengths are known in advance, for example due to prior measurement, or lie within a certain tolerance range, for example the production tolerance range in new chisels. By taking into account the holder wear thus determined, it is then also possible to determine the exact wear on the new chisel on an already worn holder. This is due to the fact that the wear on a holder is negligibly low over the service life of a chisel.

If the volume of the chisel head or a part of the chisel head, in particular the chisel tip or a part of the chisel tip, is to be determined based on the determined position value, then it is possible based on the positions of the points that represent the position value, to produce a contour line, for example, that can be used to determine an average wear volume of the chisel tip and/or the chisel head.

This wear volume can then be compared to a reference value that describes, for example, the contour line of an unworn tool. It is also possible to compare the wear volume to previously measured contour lines, which describe certain wear states and function as reference values.

A further specification of the wear state can be achieved in order to establish the reference value, the position of at least one point of the chisel, the chisel holder, and/or the chisel holder replacement system is determined in the unworn new state.

Because it can be derived, for example, from the geometric interrelationships, the reference value can be a theoretical value that is preset in a fixed way, for example the length of the chisel head used as the chisel parameter, or else it is possible for the reference value and position value to be determined in the worn or partially worn state. This method is suitable if, for example, the current wear situation is not known or because an entire roller is being replaced and is equipped with already worn chisel holders and chisels.

According to a preferred embodiment of this invention, it is also possible for a wear parameter to be correlated with the at least one position value as a reference value by a characteristic field or a functional correlation. The functional correlation or the characteristic field can be determined in advance. The characteristic field can, for example, contain experimentally determined correlations.

If the process guidance is carried out so that the position of the central longitudinal axis of the chisel head and/or chisel tip is established as a position value and this position value is compared to a reference value that contains the ideal position of the central longitudinal axis, then this permits an asymmetrical wear on the chisel to be simply detected.

In one method embodiment of this invention, the wear on the chisel and the wear on the chisel holder are determined separately from each other in an additional calculation step. This makes it possible to obtain detailed system information that gives the user an exact picture of the wear on the system components.

This can be carried out in a particularly simple way if the method first has the total wear determined based on the addition of the wear on the chisel holder and the wear on the chisel. Then, a tool replacement is performed. As the method continues, the actual position of at least one point of the chisel mounted on the worn or partially worn chisel holder must be determined in the new state. Then this measurement result is compared to a reference value of the at least one point in the new state of the chisel and chisel holder and then the wear on the chisel holder is determined through subtraction. The chisel wear is then calculated from the difference between the total wear and the holder wear.

If it is one assumed that the holder wear between two chisel replacements approaches zero, then the chisel wear can be determined at any time according to this method by using its subtraction of the holder wear from the measurement respectively preceding it.

In another method embodiment of this invention, a first reference value is established in the new state of the chisel and holder and is stored until the holder is discarded. A second reference value is established and then after each chisel replacement, is established again by a reference measurement and then stored. Then at any time, the chisel wear is determined from a measurement with a subsequent subtraction using the second reference value, the total wear is determined from a measurement with a subsequent subtraction using the first reference value, and the holder wear is determined from the difference between the second and first reference value.

Alternatively, in one embodiment of the method of this invention, the total wear is determined by comparing at least one position of the chisel tip to a reference position that was previously established in the new state.

Based on this, the total wear is determined by adding the chisel holder wear and the chisel wear. Then, the position of a second point on the chisel is compared to a corresponding reference position in the new state of the chisel. This second point is closer to the holder than the first point. The chisel holder wear is determined from it. The difference between the shift of the second point and the overall shift yields the chisel wear.

If, in order to determine the wear on the chisel holder, at least one point of the chisel shaft, which is subject to only slight wear or to no wear at all, is established as a position value and compared to the reference value of this point in the unworn or partially worn state, then the wear state of the holder can be determined directly in the tool system, without a need to carry out a reference measurement on a replaced tool.

Preferably, at least one point of an extraction groove of the chisel head is established as a position value/reference value.

The extraction groove is subject to only slight wear or to no wear at all. An exact determination of the wear is possible because the position value and/or the reference value is determined, for example, by runtime measurement, phase shifting, or triangulation. In this context, the physical effect on which the measurement principle is based is immaterial, for example it can be acoustic, optical, magnetic, or mechanical.

If the method determines the rotational position of a milling roller that supports the chisel, the chisel holder, and/or the chisel holder replacement system, it is then possible to ascertain the rotational position of the roller and based on it, the exact position of the respectively measured tool. It is then possible to specifically locate the respective chisel and to replace it as needed, for example.

BRIEF DESCRIPTION OF THE DRAWINGS

This invention is explained in greater detail below in view of exemplary embodiments shown in the drawings, wherein.

DETAILED DESCRIPTION OF THE INVENTION

Figure 1:
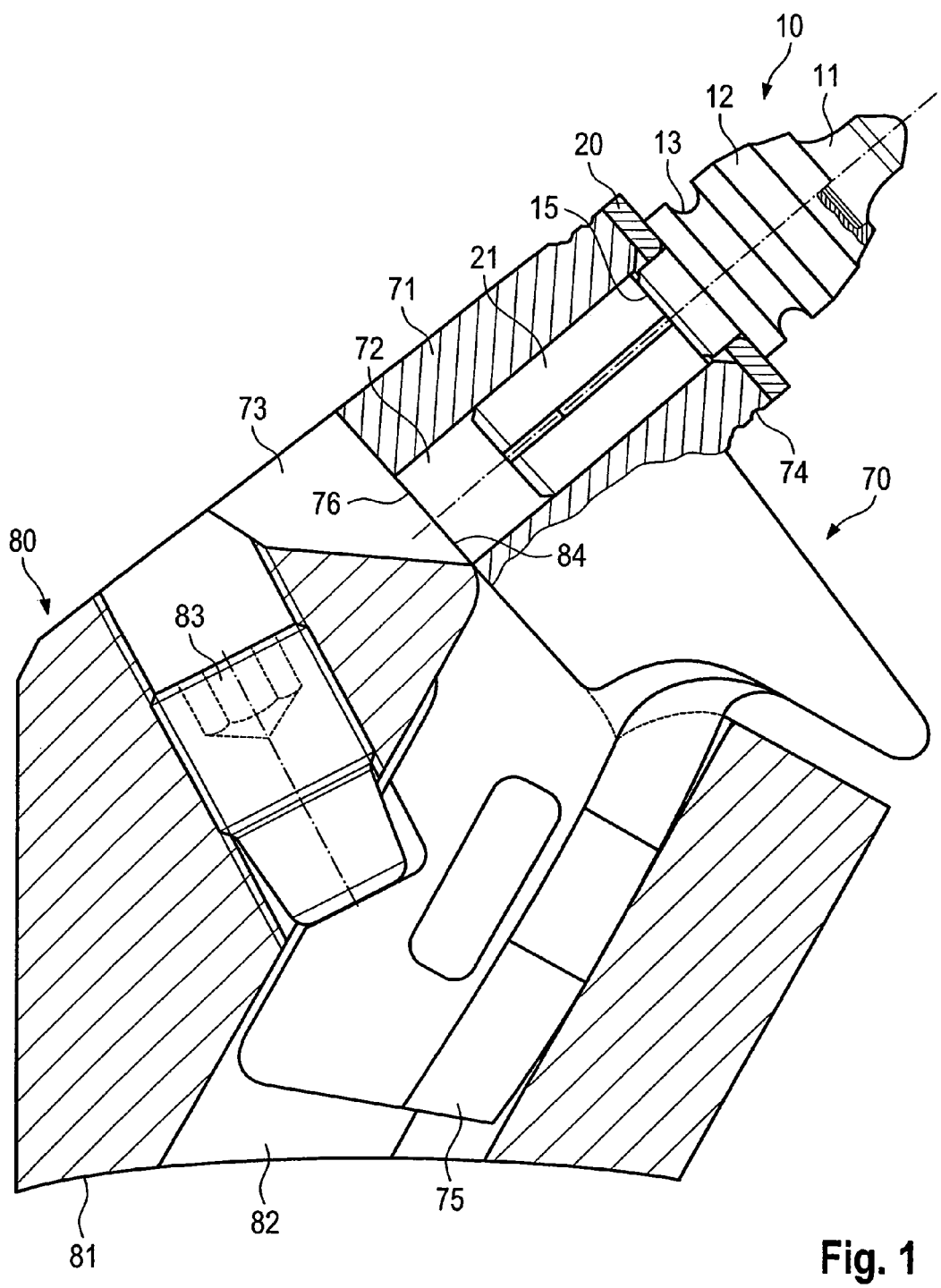
FIG. 1 shows a side view of a chisel, such as a round-shafted chisel, which is for a road surface milling machine, a mining machine, a surface miner, or the like, and is inserted into the holder of a replaceable holder tool for such machines.

FIG. 1 shows an example of a chisel 10 of the type known from the prior art and described, for example, in German Patent Reference DE 38 18 213 A1. The chisel 10 has a chisel head 12 and a chisel shaft 15 integrally formed onto the chisel head 12. The chisel head 12 supports a chisel tip 11 composed of a hard material, for example hard metal.

The chisel tip 11 is usually soldered to the chisel head 12 along a contact surface. A circumferential extraction groove 13 is in the chisel head 12. This extraction groove 13 serves as a tool receptacle because a removing tool is placed onto it, enabling removal of the chisel 10 from a chisel holder 70.

The chisel shaft 15 supports a longitudinally slit, cylindrical clamping sleeve 21. This sleeve is secured so that it cannot be detached in the direction of the longitudinal span of the chisel 10, but is able to freely rotate in the circumferential direction on the chisel shaft 15. In the region between the clamping sleeve 21 and the chisel head 12, a wear-prevention disk 20 is provided. When installed, the wear-prevention disk 20 rests against a counterpart surface of a chisel holder 70 and, on the side oriented away from the chisel holder 70, rests against the underside of the chisel head 12.

The chisel holder 70 has an attachment 71 in which a chisel receptacle 72 in the form of a cylindrical bore is provided. In the chisel receptacle 72, the clamping sleeve 21 is secured with its outer circumference clamped against the inner wall of the bore. The chisel receptacle 72 opens out into the ejection opening 73. An ejecting pin, not shown, can be inserted through this opening in order to remove the chisel 10. It acts on the end of the chisel shaft 15 so that by overcoming the clamping force of the clamping sleeve 21, the chisel 10 is slid out from the chisel receptacle 72.

As shown in FIG. 1, the attachment 71 has two circumferential grooves in a cylindrical region below the wear-prevention disk 20. The grooves serve as wear markings 74. During operational use, the wear prevention disk 20 rotates and in so doing, can produce wear, chisel holder wear, on the supporting surface of the attachment 71. When the supporting surface abrades down until it reaches the second wear marketing, the chisel holder 70 is worn down to the point that it must be replaced.

The chisel holder 70 has an insertion attachment 75 that can be inserted into an insertion receptacle 82 of a base part 80 and can be clamped there by a clamping screw 83.

The clamping screw 83 thus presses a contact surface 76 of the chisel holder 70 against a supporting surface 84 of the base part 80. In a manner not shown in detail in FIG. 1, the underside 81 of the base part 80 itself is welded to the milling roller tube of a milling roller.

Figure 2:
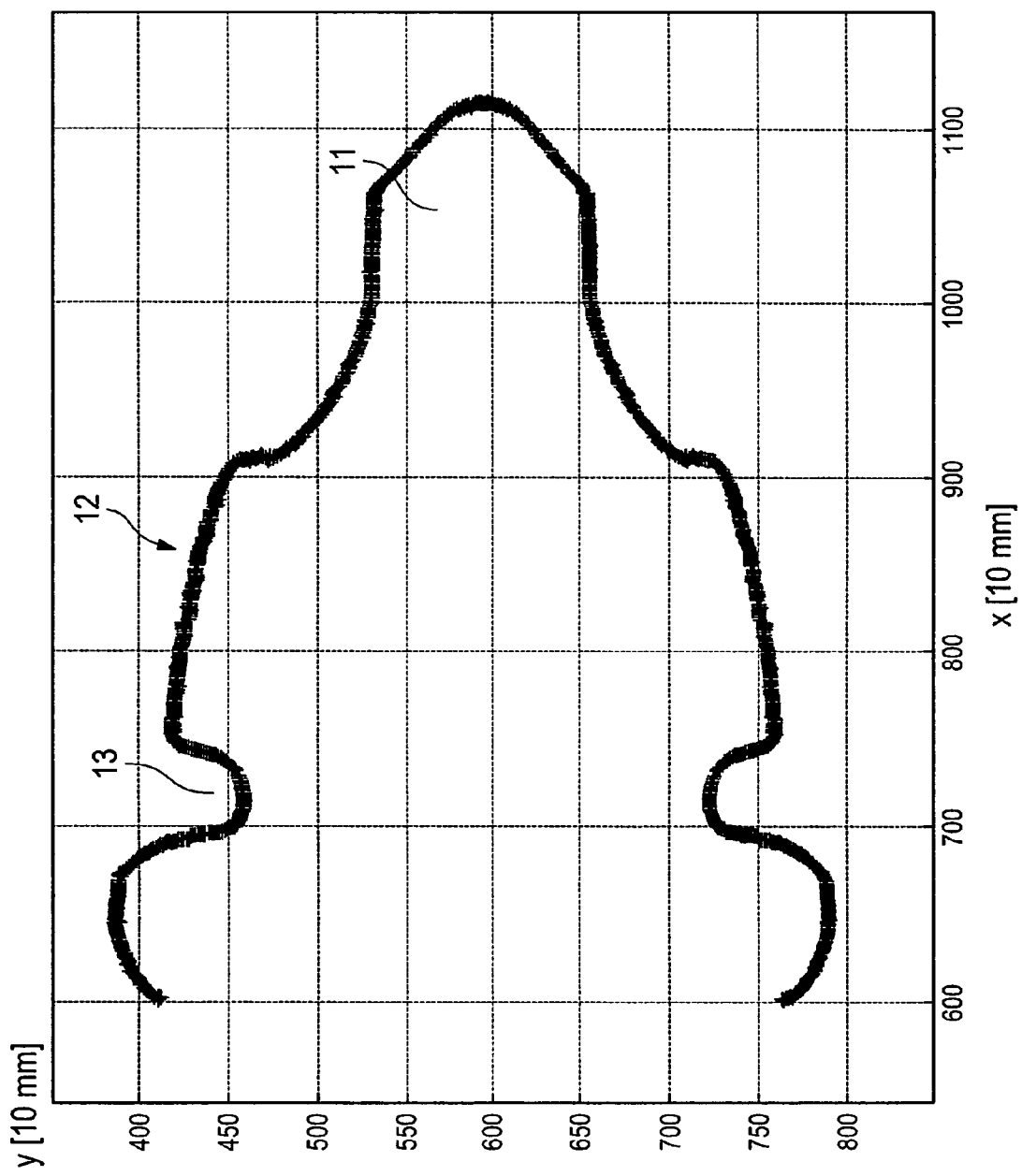
FIG. 2 shows the chisel head of the chisel from FIG. 1, shown in a graph.

To determine the wear state of the chisel 10 mounted on the chisel holder, a contactless measurement of the chisel head 12 is performed. In this instance, a specified point or a plurality of points of the chisel head 12 each is measured and/or determined as position values. FIG. 2 shows the contour of an unworn chisel head 12, in a side view. This contour is shown in a graph, with the span of the chisel head 12 in the direction of the longitudinal axis of the chisel 10, the x-axis, plotted over the span in the width direction, perpendicular to the central longitudinal axis, such as the y-axis. The contour of the chisel head 12, including the chisel tip 11, is composed of a multitude of measured points. The linear border or contour line represents an interpolation of these position values.

Figure 9:
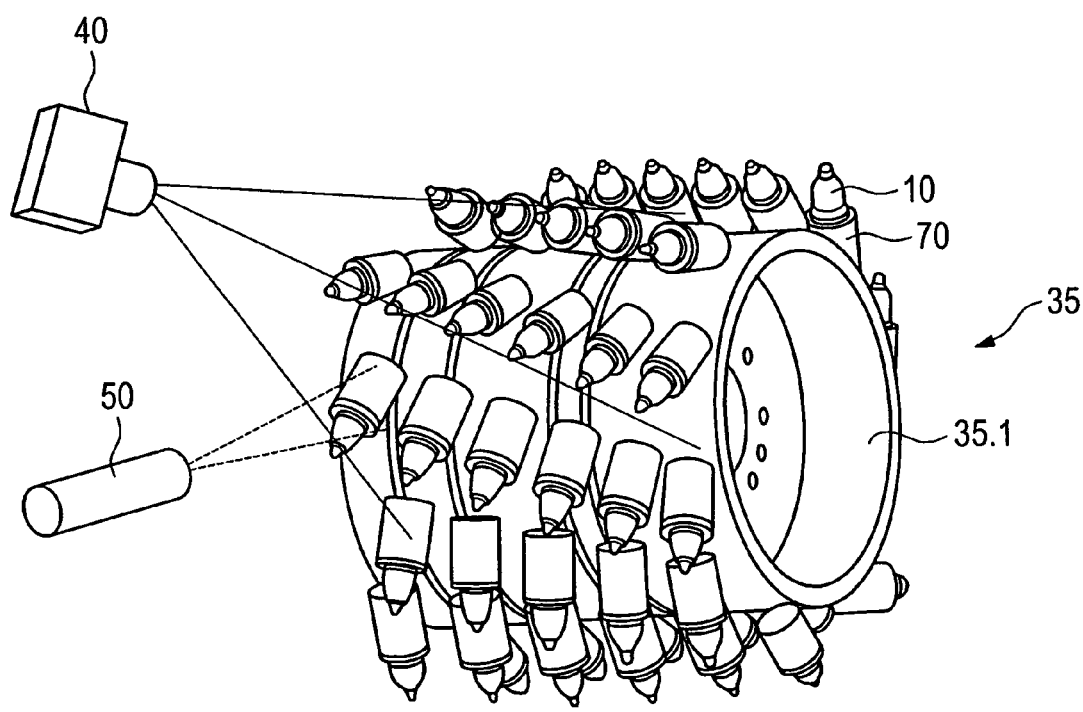
FIG. 9 shows a milling roller of the road surface milling machine according to FIG. 8, with a measuring device that functions based on the principle of triangulation.
Figure 10:
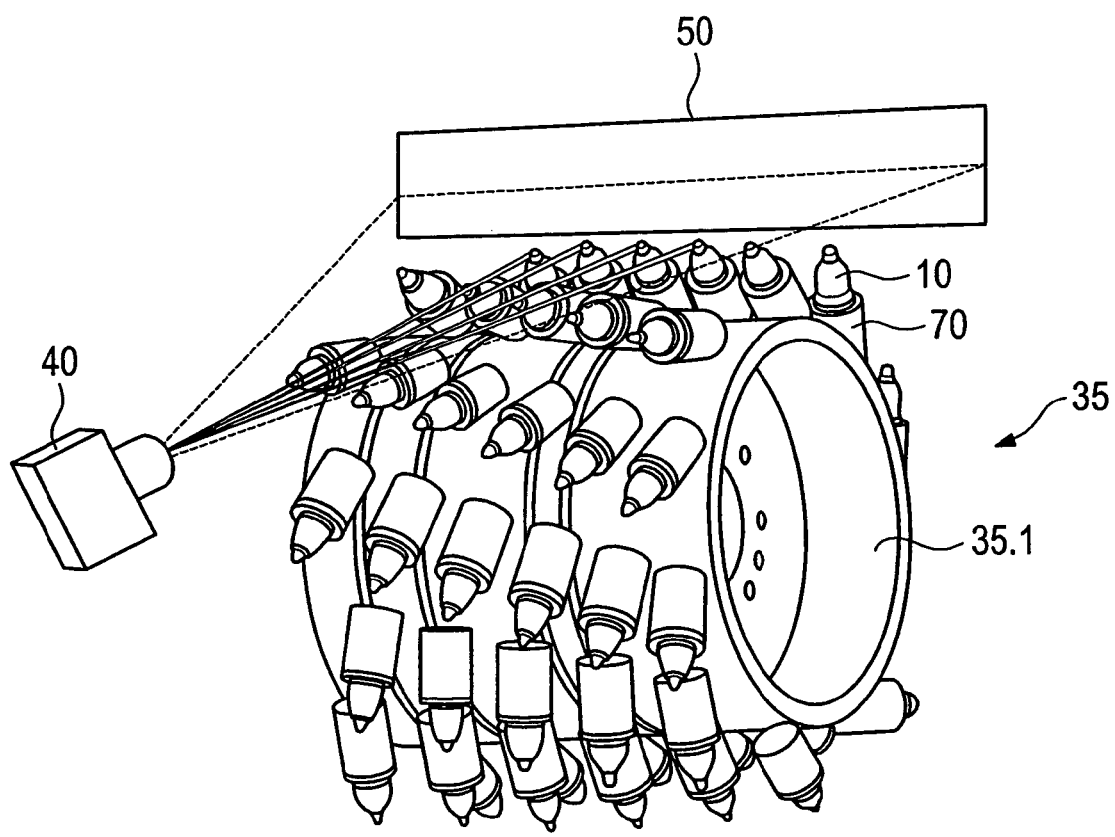
FIG. 10 shows the milling roller according to FIG. 9, with an alternative embodiment of the measuring device that functions based on a shadow-casting method.

The measurement on a milling roller 35, as shown in FIGS. 9 and 10, can be performed when the chisel 10 is in the unworn state or in a partially worn state. Then these points, such as the calculated chisel head contour, or also only a single measurement point can be determined and stored as reference values or as a reference value in a memory device.

Figure 3:
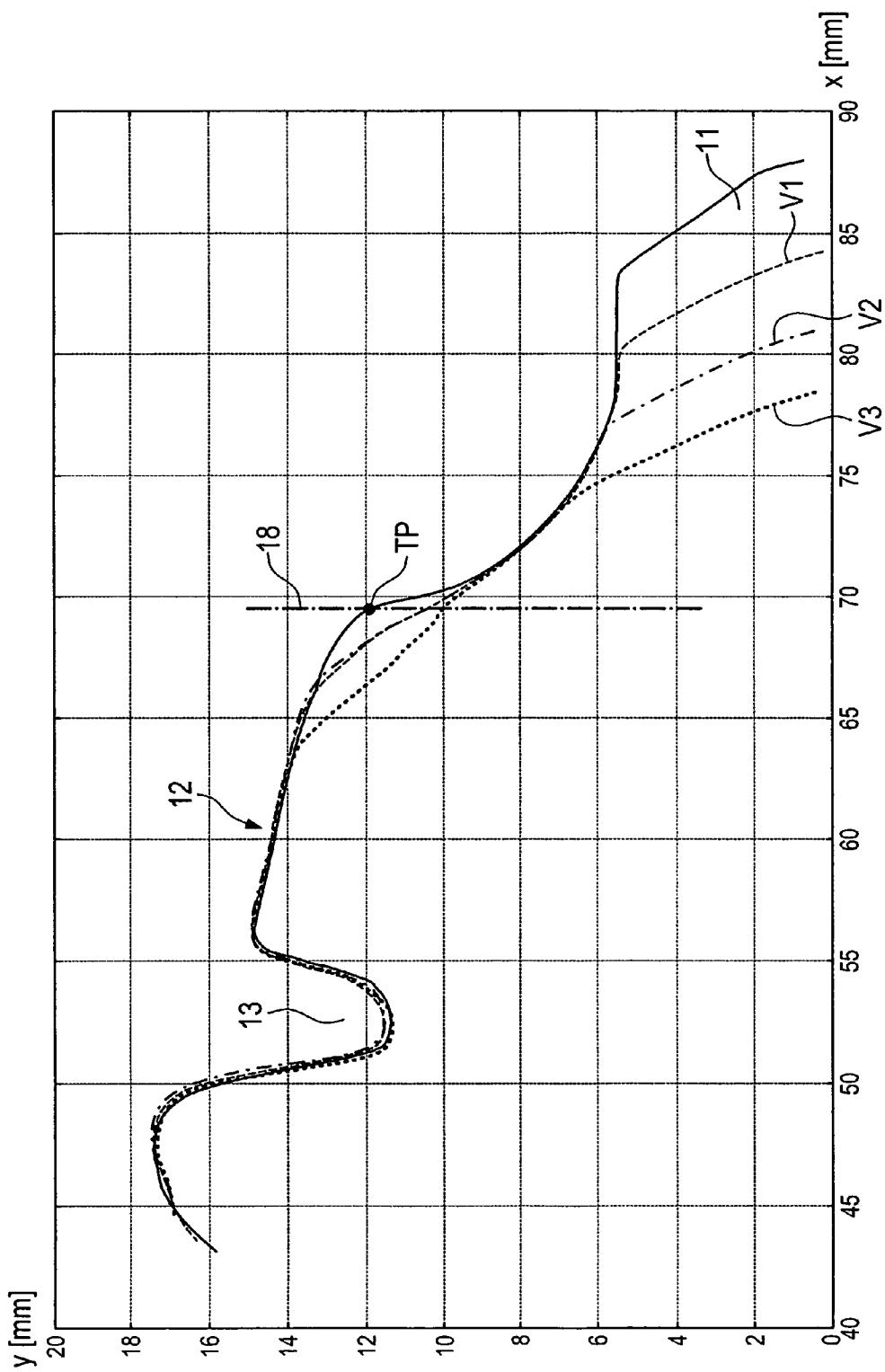
FIGS. 3 through 7 show various wear states of the chisel head, depicted in graphs.

FIG. 3 shows various measurement images of a chisel 10. The chisel head 12 here is shown in the unworn state and in three measured wear states V1 through V3. The wear state V3 represents the state in which the chisel 10 is no longer suitable for further operation and must be replaced. The wear can be determined by comparing the reference value, the contour in the unworn state, to the respectively measured current chisel head contour, such as wear states V1, V2, or V3, that represent the position value.

The contours must be aligned with one another. Due to holder wear or other error sources, unworn contour regions are not necessarily situated at the same absolute positions, such as relative positions in relation to the rotational axis of the roller. Setting the contours into relation with one another again requires reference features that are clearly identifiable and appear in both the unworn and worn state, thus permitting an alignment and an exclusive evaluation. The extraction groove 13, the wear markings 74, the wear-prevention disk 20, or other prominent regions that are subject to only slight wear or to no wear at all can be used as reference features.

As shown in FIG. 3, the length of the chisel head 12 decreases during operational use. Through subtraction of the contour lines in a switching unit, it is possible to obtain information about the wear state, which is visually depicted for the user on a display unit, for example. Instead of measuring the entire contour of the chisel head 12, it is also possible for only a part of the contour or a single point, in particular the front end of the chisel tip 11, to be detected as a position value. More detailed information about the wear state can be obtained if the wear on the chisel tip 11 and on the chisel head 12, without the chisel tip 11, are determined separately.

This is easily possible with the previously known position of the attachment, such as the attachment point TP/attachment line 18, of the chisel tip 11 to the chisel head 12 in the unworn state.

Figure 4:
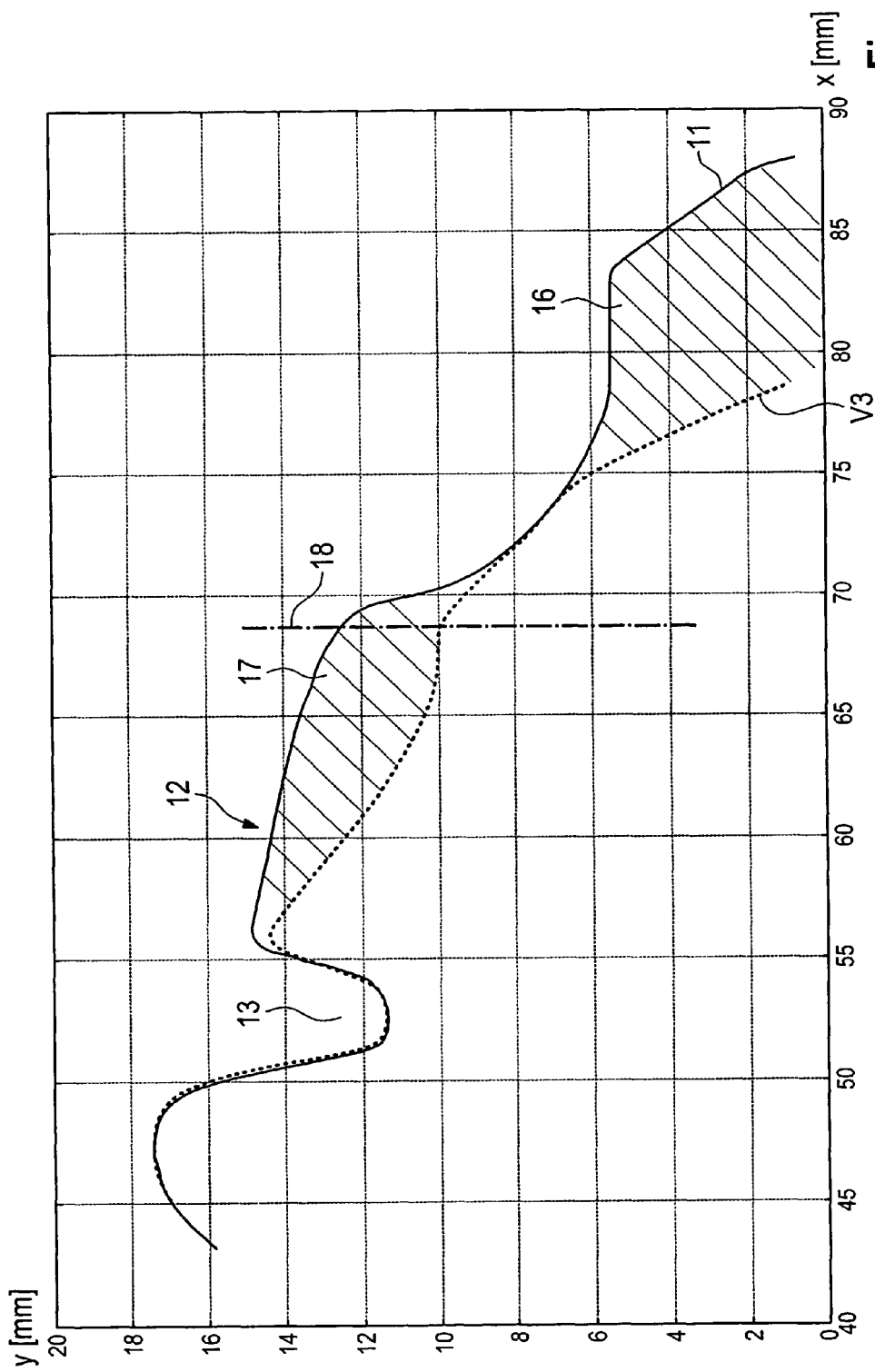

If the measured wear states V1 through V3 are superimposed on the unworn contour of the chisel head 12, as shown in FIG. 2, then the total wear volume can be determined through integration of the measured contours along the x-axis. In FIG. 4, the wear volume is depicted as a shaded region.

Consequently, the wear volume can be used as a position value and compared to a reference value. The reference value in this case can comprise a functional correlation or a characteristic field. Different wear volumes are correlated with associated wear states, for example a $mm^3$ of wear volume corresponds to b % wear. Based on the previously known position of the attachment point TP/attachment line 18, the tip wear 16 and the head wear 17 can then be separately determined through subtraction. This wear determination gives the user qualitative information, for example, about whether the chisel 10 is still suitable for certain milling tasks. Thus, a chisel that has not in fact reached its wear limit yet, but does have a certain degree of tip wear, can no longer be used for fine milling work, for example.

In the method according to FIGS. 3 and 4, the measured position values are superimposed with the reference values.

During the machining process, wear occurs not only on the chisel head 12, but also on the chisel holder. The chisel holder wears down in the direction of the central longitudinal axis of the chisel 10. The isolated determination of the longitudinal wear on the chisel holder in this direction then succeeds simply because the degree of shifting of the position value toward the reference value required to reach the superimposed positions shown in FIGS. 3 and 4, shifting of the chisel head 12 in the direction of the x-axis until, for example, the extraction grooves of the individual wear states are congruent, constitutes an absolute wear value of the chisel holder. The total shifting of the chisel tip 11 minus this wear value is then a separate indication of the chisel wear.

Figure 5:
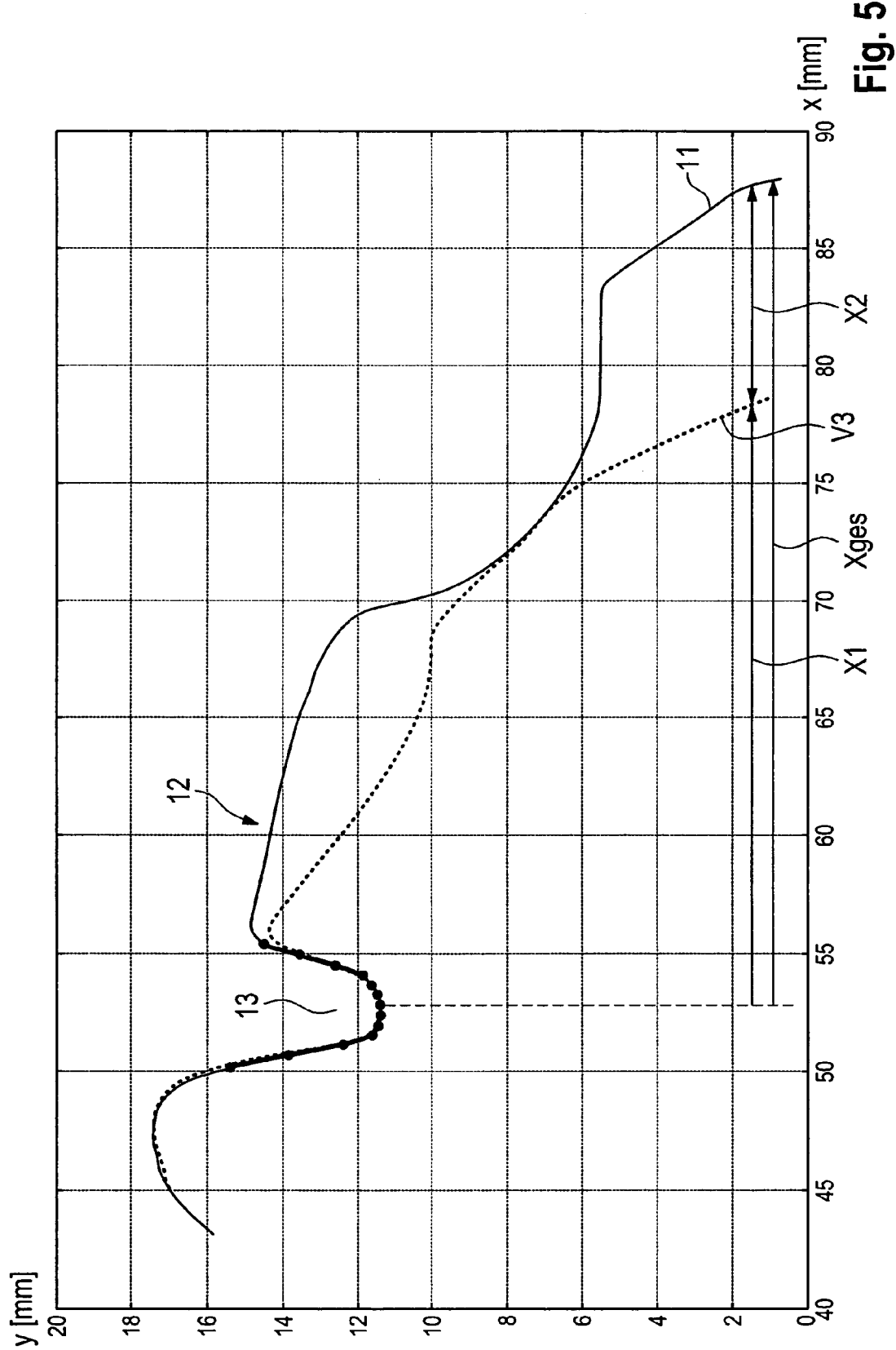

FIG. 5 shows a method variant in which information about wear is obtained based on measuring a clearly identifiable feature on the chisel. The feature and the surroundings of this feature should be subject to only slight wear or to no wear at all. According to FIG. 5, the extraction groove 13, a part of the extraction groove 13, or a point, for example the groove bottom, of the extraction groove 13 is used as a definite feature and reference criterion.

Furthermore, this feature is then used for determining the distance to the position of the free end of the chisel tip 11, such as the position value. This makes it easily possible to determine the longitudinal wear in a simple way. If the position of the chisel tip 11 is known, then as described above, it is once again possible to determine the chisel holder wear. Alternatively or in addition, as specified in conjunction with FIG. 4, it is also possible to determine the volume wear and the associated wear lengths, such as where X=total wear.

The relative measurement through the use of a definitely identifiable feature as a reference point has the advantage that a wear determination can also be made in the absence of a reference measurement because, for example, the length of the replaced chisel 10 or the wear state of the chisel 10 or chisel holder is not known.

Figure 6:
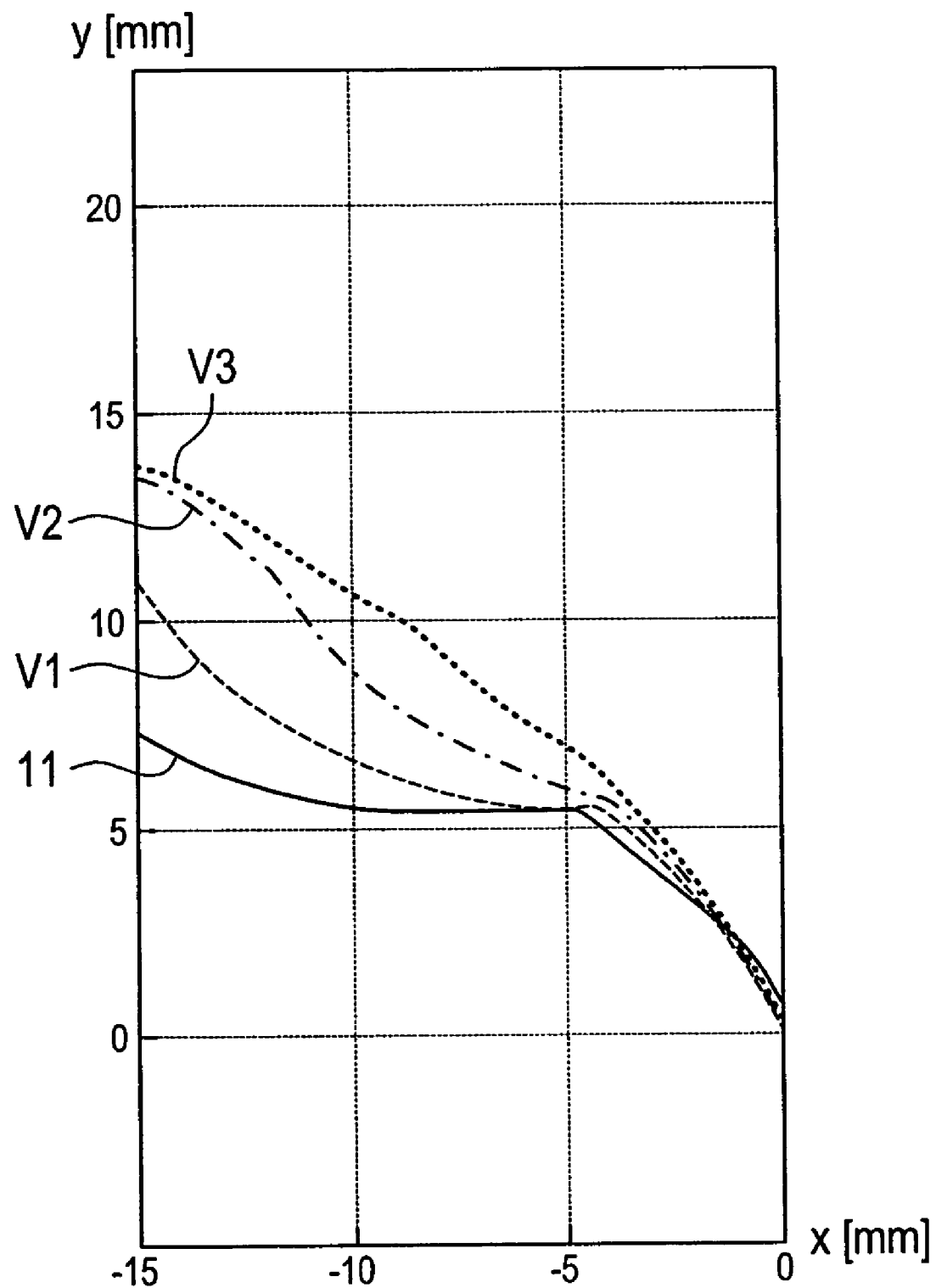

FIG. 3 shows the change in the chisel head contour as the wear increases. The decreasing length of the chisel head 12 is clearly visible. If the chisel head contours are respectively shifted toward the point of the maximum length of the chisel 10, such as shown in FIG. 6, then through the changing head angle the angle becomes flatter as chisel wear increases and through the increasing volume of the chisel head 12 the increasing wear state of the chisel 10 becomes evident when the area under the contour curve, starting from the respective tip over a certain length, is integrated. It is thus possible to establish a functional correlation between the head volume/area and the absolute chisel length for a certain chisel type, for example by experiments carried out in advance to determine reference values.

If this correlation is known, then the length of the chisel 10 can be determined through measurement/integration of the respective head volume currently present. This method, however, is based on the assumption that the chisel tip 11 has a cross-section that increases in the longitudinal direction of the chisel. The integration method is preferably established so that even with completely worn chisels 10, the integration does not extend into the head region because erosion in the head region distorts the result.

This method has the advantage of not requiring a reference point that is subject to little wear. Sometimes such a reference point is not present or is very difficult to identify.

Figure 7:
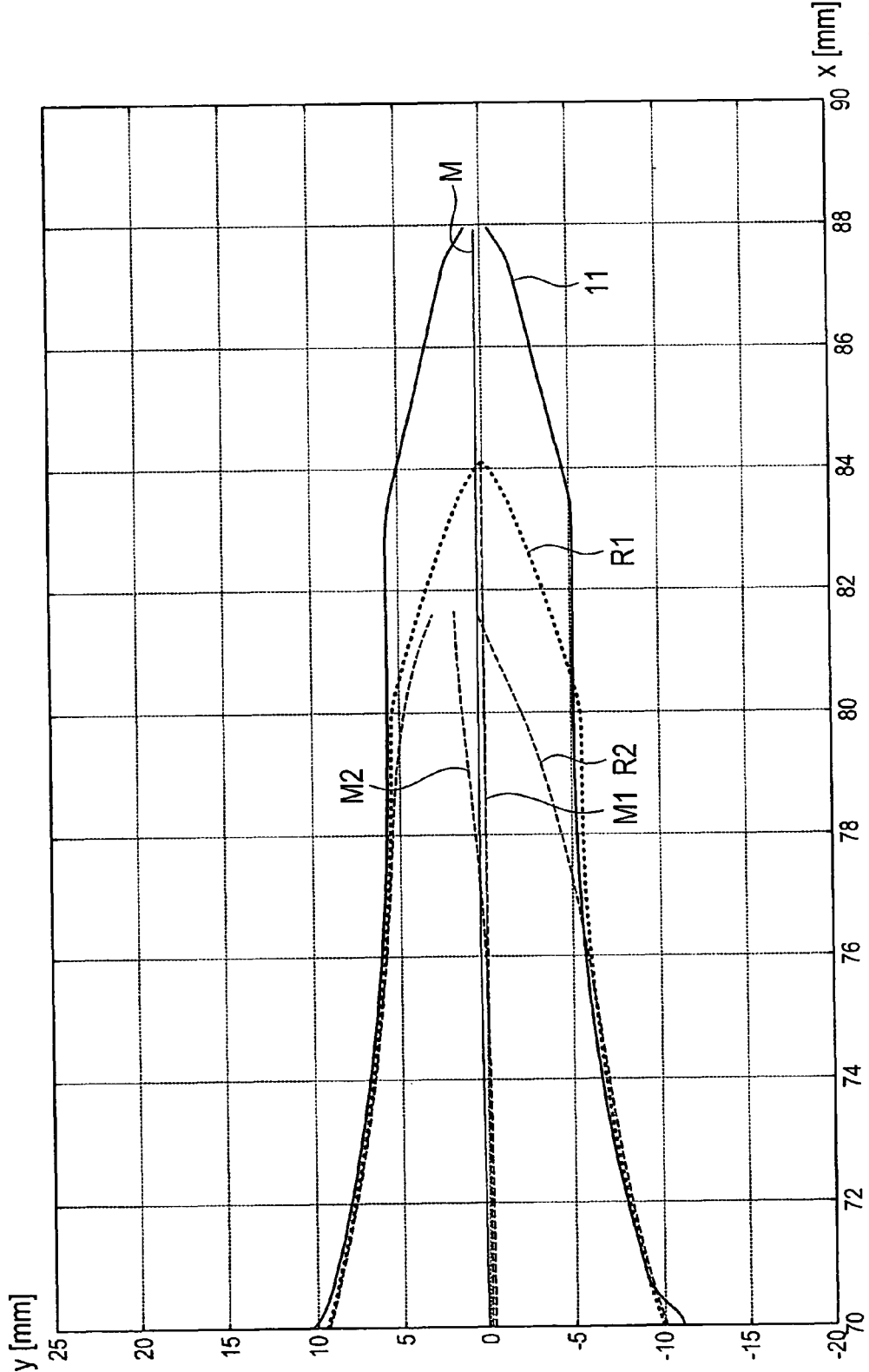

In order to determine the asymmetry factor of the wear, it is possible, for example, to calculate the average between the upper and lower contour lines. FIG. 7 shows the contour lines and their averages for a new chisel tip 11, for a chisel tip 11 with rotationally symmetrical wear R1, and for a chisel tip 11 with non-rotationally symmetrical wear R2. It is clear that with the asymmetrically worn chisel 10, the average line M2 of the two contour lines has a certain slope in relation to the longitudinal axis of the chisel. The angular position could be easily evaluated in order to determine the asymmetry factor of the wear. It is also possible, however, to directly ascertain/determine the position/deviations of several contour lines.

According to the same method, it is possible to determine an asymmetrical wear on the chisel head 12. Usually, however, an asymmetrically worn chisel head 12 is accompanied by an asymmetrically worn chisel tip 11. It is thus sufficient to analyze the chisel tip 11.

Figure 8:
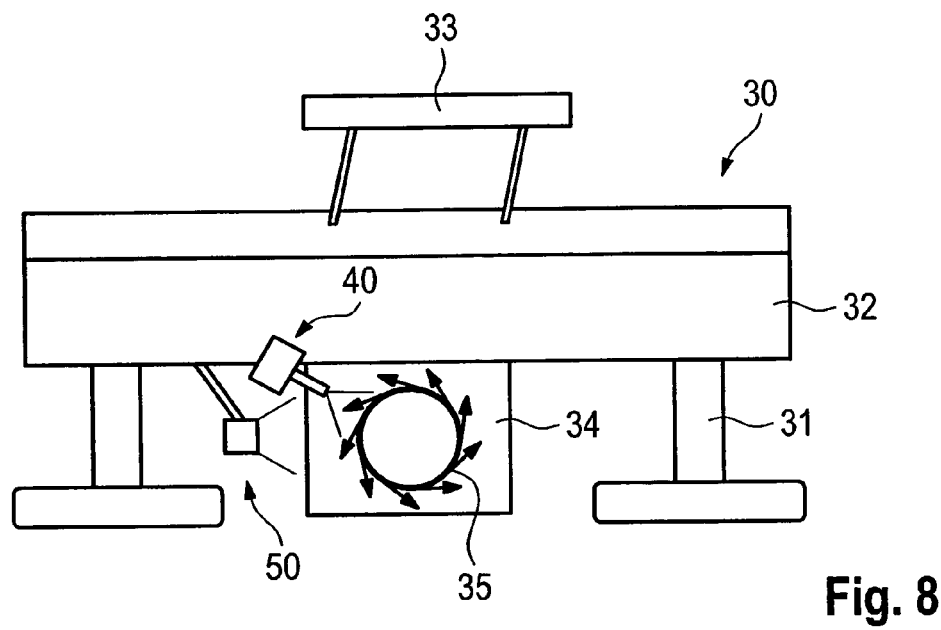
FIG. 8 is a schematic side view of a road surface milling machine.

FIG. 8 symbolically depicts a road surface milling machine 30 in which a machine body 32 is supported by four column-like traveling units 31. The road surface milling machine 30 can be controlled from a control center 33. A milling roller 35 is mounted in a milling roller housing 34.

In order to measure the wear state using one of the above-described methods, a light source 50 and a camera 40 are associated with the milling roller 35. The milling roller 35 is shown in greater detail in FIG. 9. Numerous chisel holder replacement systems, each having a respective chisel holder 70, are fastened to the surface of a milling roller tube 35.1 of the milling roller 35. A chisel 10 is mounted in each chisel holder 70. In the current example, the chisel holders 70 are welded directly to the milling roller 35.

It is possible to use the chisel holder replacement system according to FIG. 1. Then, the base part 80 is welded to the milling roller 35.

As the apparatus for measuring the chisel contours, an optical system is used in which a type of scanning operation is used to measure a contour line of the roller surface. The measurement principal used here can, for example, be a tri-angulation method in which the roller surface is illuminated for example by a light source 50 such as a laser line. The laser line produced in this way is observed by a camera 40 at a different angle, as a result of which height differences on the roller surface, for example produced by the chisels 10, produce shifts in these projection lines. With a known differential angle between the camera 40 and the light source 50, it is possible to calculate the height coordinates. By rotating the milling roller 35, it is thus possible to establish a height profile of the circumference surface of the roller, from which the contour line of the individual chisels 10 can be read.

Another optical measurement principal for measuring the height and/or geometry of the chisels 10 is the shadow-casting method according to FIG. 10. This method takes advantage of the fact that as they move through a light curtain produced by a light source 50, the chisels 10 produce a shadow contour that can be observed by a camera 40 and evaluated. The significant advantage of this method is that it is possible to work with a single camera line using the same principle as a document scanner. It is thus possible, even for measurements of milling rollers 35 with large diameters and high rotation speeds, to be carried out with a sufficient resolution.

According to an alternative embodiment of this invention, it is possible to modify the method described in relation to FIG. 10. In this case, a light curtain in the form of a light plane is again produced by the light source 50. This light plane extends parallel to the central longitudinal axis of the milling roller 35 and tangential to the roller surface. In this case, the light plane is oriented so that when the milling roller 35 rotates, the chisel tips of the chisels 10 initially pass through the light plane.

They then throw shadows that can be detected by the camera 40. The chisels 10 are conveyed across the light plane over a certain rotation angle of the roller until they dip below the light plane again.

A reference measurement can be performed with unworn chisels 10 and/or chisel holders 70. In this case, the time at which the chisel 10 passes through the light plane, an entry or exit, is detected and the associated rotation angle of the milling roller 35 is detected. After an operational use, a corresponding measurement is carried out on the worn or partially worn chisel 10. Due to the reduction in length, the chisel 10 breaks through the light plane later and dips below it earlier in comparison to an unworn system. The corresponding rotation angles of the milling roller 35 can then be determined as position values. The rotation angles are then compared to the rotation angles of the unworn system, such as reference values. It is then possible to calculate the wear state through subtraction using the differential angle or the differential angle is used directly as a wear criterion.

During the milling process, the measurement system is suitably stowed in a corresponding protective device during phases in which no measurement is performed. When a second camera 40 is used, it is possible, for example, to perform a direct measurement of the height geometry without an additional light source.

Alternatively, through appropriate positioning of a second camera, additional measurements of the contours can be performed, thus increasing the overall information density and increasing the probability of detecting asymmetrical wear states.

Alternatively, the position of the chisel tip 11 and the position of the chisel head contour can also be detected in at least one step by other distance-measuring sensors, for example ultrasonic sensors, proximity switches.

German Patent Reference 10 2008 045 470.2, filed 3 Sep. 2008, the priority document corresponding to this invention, to which a foreign priority benefit is claimed under Title 35, United States Code, Section 119, and its entire teachings are incorporated, by reference, into this specification.

What is claimed is:

1. A method for determining a wear state of a milling tool including a chisel, the method comprising;
   determining using a distance measuring sensor a position value of at least one point on the chisel by either measuring or calculating the position value; and
   comparing the position value in a switching unit to at least one reference value stored in a memory device to determine the wear state of the milling tool.

2. The method as recited in claim 1, wherein a contactless measurement method or an optical measurement method is used to determine the position value.

3. The method as recited in claim 2, wherein a tip position of a chisel tip is used as the position value.

4. The method as recited in claim 1, further comprising:
   determining an other position value of at least one additional point on the chisel that is subject to only slight wear or to no wear, the other position value being the at least one reference value; and
   determining chisel wear based on a difference between the position value and the reference value.

5. The method as recited in claim 1, wherein to establish a chisel head surface or a part of the chisel head surface as the position value, a plurality of points or a contour of the chisel surface, or a partial contour of a part of the chisel head surface is used.

6. The method as recited in claim 5, wherein based on the position value established, a volume of a chisel head or of a part of the chisel head or of a chisel tip, or of a part of the chisel tip is determined.

7. The method as recited in claim 1, wherein the chisel includes a chisel head and a chisel tip, and a first wear state of the chisel head without the chisel tip and a second wear state of the chisel tip alone are separately determined by a position value comparison.

8. The method as recited in claim 1, wherein a position value of at least one point of the chisel or of a chisel holder in an unworn new state is determined to establish the at least one reference value.

9. The method as recited in claim 1, wherein a tool parameter is stored or is storable as the at least one reference value.

10. The method as recited in claim 1, wherein the at least one reference value and/or the position value each is determined in a worn state or a partially worn state.

11. The method as recited in claim 1, wherein the position value is correlated with a wear parameter as a reference value by a functional correlation.

12. The method as recited in claim 1, wherein the chisel includes a chisel head and a chisel tip, and an axis position of a central longitudinal axis of the chisel head and/or the chisel tip is determined as the at least one position value and the at least one position value is compared to a reference value that contains an ideal position of the central longitudinal axis.

13. The method as recited in claim 1, wherein wear on the chisel and wear on a chisel holder are determined separately from each other in an additional calculation step.

14. The method as recited in claim 13, wherein first a total wear is determined based on an addition of a first wear on the chisel holder and a second wear on the chisel, then the chisel is replaced with a new chisel, an actual position of at least one point of the new chisel is determined in the new state, and then a measurement result is compared to a reference value of at least one point of the new chisel and the chisel holder and then the first wear on the chisel holder is determined through subtraction.

15. The method as recited in claim 14, wherein the second wear on the chisel is determined through subtraction, using the total wear and the holder wear.

16. The method as recited in claim 15, wherein the holder wear from a preceding measurement is used for the subtraction to determine the second wear on the chisel.

17. The method as recited in claim 13, wherein a first reference value is determined in the new state of the chisel and holder, a second reference value is established, which second reference value is updated by a new reference measurement after each chisel replacement, and the holder wear is determined based on the first and second reference values.

18. The method as recited in claim 17, wherein a position value on a worn chisel is determined, the total wear is determined through subtraction using the first reference value, and the chisel wear is determined through subtraction using the second reference value.

19. The method as recited in claim 13, wherein a first reference point on a chisel tip and a second reference point closer to the holder are established, then a first position value at the first reference point and a second position value at the second reference point are determined, and the total wear is determined through subtraction using the first position value and the reference value, and holder wear is determined through subtraction using the second position value and the reference value.

20. The method as recited in claim 13, wherein to determine the wear on the chisel holder, the at least one point of the chisel, is subject to only slight wear or to no wear, and the at least one point of the chisel is established as a position value and compared to the reference value of the at least one point in the unworn state or the partially worn state.

21. The method as recited in claim 1, wherein at least one groove point of an extraction groove of the chisel is established as the position value and/or the reference value.

22. The method as recited in claim 1, wherein the position value and/or the reference value each is determined by a runtime measurement, a phase shifting, or a triangulation.

23. The method as recited in claim 1, wherein a rotational position of a milling roller that supports the chisel is determined.

24. The method as recited in claim 1, wherein both the reference value and the position value are correlated with a rotation angle of the milling roller and a tool wear state of the milling tool is determined based on a calculation using the rotation angle.

25. The method as recited in claim 1, wherein:
in the determining step, the distance measuring sensor is selected from the group consisting of a camera, an ultrasonic sensor and a proximity switch.

26. The method as recited in claim 1, wherein:
in the determining step, the distance measuring sensor operates upon a measurement principle selected from the group consisting of acoustic measurement, optical measurement, magnetic measurement and mechanical measurement.

27. A method for determining a wear state of a milling tool mounted on a milling roller of a milling machine, using a measurement system mounted on the milling machine, the measurement system including a measuring sensor, the method comprising:
(a) determining a position value of at least one point on the milling tool using the measuring sensor of the measurement system; and
(b) determining the wear state of the milling tool by comparing the position value to a reference value.

28. The method of claim 27, wherein the position value defines a position in space relative to the milling machine.

29. The method of claim 27, wherein:
step (a) comprises determining the position value using an optical measurement.

30. The method of claim 27, wherein:
step (a) comprises determining the position value without contacting the point on the milling tool.

31. The method of claim 27, wherein the milling tool includes a chisel head and a chisel tip, and wherein:
step (a) comprises determining the position value of a tip position of the chisel tip.

32. The method of claim 27, wherein:
in step (b), the reference value is a previously determined position value of a point on the milling tool that is subject to only slight wear or no wear.

33. The method of claim 27, wherein:
step (a) comprises determining a plurality of position values of a plurality of points on the milling tool; and
step (b) comprises determining a volume of at least a portion of the milling tool based on the plurality of position values.

34. The method of claim 27, wherein the milling tool includes a chisel head and a chisel tip wherein:
step (b) comprises determining a first wear state of the chisel head and a second wear state of the chisel tip.

35. The method of claim 27, wherein the milling tool includes a chisel and a chisel holder, wherein:
step (b) comprises separately determining the wear state of the chisel and the wear state of the chisel holder.

36. The method of claim 27, wherein:
in step (b) the reference value is a previously determined position value of at least one point on the milling tool in an unworn new state.

37. The method of claim 27, wherein:
in step (b) the reference value is a previously determined position value of at least one point on the milling tool in a worn state.

38. The method of claim 27, wherein the milling tool includes a chisel and a chisel holder, the method further comprising:
determining a first position value of a first point on a new first chisel in a new first chisel holder;
determining total wear on the first chisel in a worn state and the first chisel holder in a worn state;
replacing the worn first chisel with a new second chisel received in the worn first chisel holder;
determining a second position value of a second point on the new second chisel corresponding to the first point on the new first chisel; and
determining wear on the first chisel holder by subtracting the second position value from the first position value.

39. The method of claim 38, further comprising:
determining wear on the second chisel by determining total wear on the second chisel and the first chisel holder, and subtracting the wear on the first chisel holder.

40. The method of claim 27, wherein the milling tool includes a chisel received in a chisel holder, the chisel including a chisel tip, the method further comprising:
determining a first position value of a first point on the chisel tip;
determining a second position value of a second point on the chisel closer to the chisel holder than the first point; and
determining total wear on the chisel and the chisel holder by comparing the first position value to the reference value.

41. The method of claim 40, further comprising:
determining wear on the chisel holder by comparing the second position value to the reference value.

42. The method of claim 41, further comprising:
determining wear on the chisel by subtracting the wear on the chisel holder from the total wear.

43. The method of claim 27, wherein:
in step (a), the measuring sensor is selected from the group consisting of a camera, an ultrasonic sensor and a proximity switch.

44. The method of claim 27, wherein:
in step (a), the measuring sensor operates based upon a measurement principle selected from the group consisting of acoustic measurement, optical measurement, magnetic measurement and mechanical measurement.

* * * * *